US010359316B1

(12) United States Patent
Han et al.

(10) Patent No.: US 10,359,316 B1
(45) Date of Patent: Jul. 23, 2019

(54) FIBER OPTIC BOLOMETER

(71) Applicants: NUtech Ventures, Inc., Lincoln, NE (US); UT-Battelle, LLC, Oak Ridge, TN (US)

(72) Inventors: Ming Han, Lincoln, NE (US); Matthew L. Reinke, Rydal, PA (US)

(73) Assignees: NUtech Ventures, Inc., Lincoln, NE (US); UT-Battelle, LCC, Oak Ridge, TN (US)

( * ) Notice: Subject to any disclaimer, the term of this patent is extended or adjusted under 35 U.S.C. 154(b) by 35 days.

(21) Appl. No.: 15/617,801

(22) Filed: Jun. 8, 2017

Related U.S. Application Data

(60) Provisional application No. 62/347,148, filed on Jun. 8, 2016.

(51) Int. Cl.
  *G01J 5/08* (2006.01)
  *G01N 21/41* (2006.01)
  *G01N 21/45* (2006.01)
  *G01N 21/47* (2006.01)
  *G01J 3/45* (2006.01)
  *G01B 9/02* (2006.01)

(52) U.S. Cl.
  CPC ........... *G01J 5/0853* (2013.01); *G01J 5/0821* (2013.01); *G01N 21/412* (2013.01); *G01N 21/474* (2013.01); *G01N 2021/458* (2013.01); *G01N 2021/4742* (2013.01)

(58) Field of Classification Search
  CPC .......... G01J 3/26; G01J 5/0821; G01J 5/0853; G01F 1/661; G01N 21/412; G01N 21/474; G02B 6/29359
  See application file for complete search history.

(56) References Cited

U.S. PATENT DOCUMENTS

| 5,286,976 A | * | 2/1994 | Cole | ........................ H01L 27/16 |
| | | | | 250/338.1 |
| 5,550,373 A | * | 8/1996 | Cole | ......................... G01J 3/02 |
| | | | | 250/338.1 |

(Continued)

OTHER PUBLICATIONS

Dong, Bo et al. "Two-wavelength quadrature multipoint detection of partial discharge in power transformers using Fabry-Perot acoustic sensors". Fiber Optic Sensors and Applications IX, Proc. of SPIE vol. 8370, 2012, pp. 83700K-1-83700K-11. (Year: 2012).*

(Continued)

*Primary Examiner* — Michael A Lyons
(74) *Attorney, Agent, or Firm* — Greer, Burns & Crain, Ltd.; Peter P. Fallon

(57) ABSTRACT

The present disclosure is directed to a fiber optic bolometer device. In an implementation, a fiber optic bolometer device includes an optical fiber and a silicon layer that comprises a Fabry-Pérot interferometer. The silicon layer includes a first surface and a second surface. The fiber optic bolometer device includes a reflective dielectric film disposed over the first surface of the silicon layer where the reflective dielectric film is adjacent to an end face of the optical fiber. The fiber optic bolometer device also includes an absorptive coating disposed over the second surface of the silicon layer (e.g., the surface distal to the end face of the optical fiber).

20 Claims, 14 Drawing Sheets

(56) References Cited

U.S. PATENT DOCUMENTS

| | | | | |
|---|---|---|---|---|
| 5,584,117 | A * | 12/1996 | Lee | G01J 3/26 216/16 |
| 6,925,213 | B2 * | 8/2005 | Boyd | G01D 5/268 385/12 |
| 7,762,720 | B1 * | 7/2010 | Zhu | G01J 5/08 374/121 |
| 7,968,846 | B2 * | 6/2011 | Talghader | G01J 3/26 250/338.1 |
| 9,995,628 | B1 * | 6/2018 | Han | G01P 5/26 |
| 2005/0151975 | A1 * | 7/2005 | Melnyk | G01B 11/18 356/480 |
| 2010/0193706 | A1 * | 8/2010 | Shen | G01J 3/26 250/474.1 |

OTHER PUBLICATIONS

Liu, Guigen et al. "High-resolution and fast-response fiber-optic temperature sensor using silicon Fabry-Perot cavity". Optics Express, vol. 23, No. 6, Mar. 23, 2015, pp. 7237-7247. (Year: 2015).*
Reinke, M. L. et al. "Development of plasma bolometers using fiber-optic temperature sensors". Review of Scientific Instruments, 87, 11E708, Aug. 8, 2016, pp. 11E708-1-11E708-4. (Year: 2016).*
Bandyopadhyay et al., "Ultrahigh-temperature regenerated gratings in boron-codoped germanosilicate optical fiber using 193 nm", Optics Letters, vol. 33, No. 16, Aug. 15, 2008.
Berthold et al., "Reflective fiber optic temperature sensor using silicon thin film", Optical Engineering, vol. 30, No. 5, pp. 524-528, May 1991.
Born et al., "Principles of optics: Electromagnetic theory of propagation, interference and diffraction of light", Seventh (Expanded) Edition, Cambridge University Press, 1999.
Choi et al., "Cross-talk free and ultra-compact fiber optic sensor for simultaneous measurement of temperature and refractive index", Optics Express, vol. 18, No. 1, pp. 141-149, Jan. 4, 2010.
Choi et al., "Miniature fiber-optic high temperature sensor based on a hybrid structured Fabry-Perot interferometer", Optics Letters, vol. 33, No. 21, pp. 2455-2457, Nov. 1, 2008.
Cocorullo et al., "A Temperature All-Silicon Micro-Sensor Based on the Thermo-Optic Effect", IEEE Transactions on Electron Devices, vol. 44, No. 5, pp. 766-774, May 1997.
Coviello et al., "Thermally stabilized PCF-based sensor for temperature measurements up to 1000 degrees C", Optics Express, vol. 17, No. 24, pp. 21551-21559, Nov. 23, 2009.
Ding et al., "Fast-Response High-Temperature Microfiber Coupler Tip Thermometer", IEEE Photonics Technology Letters, vol. 24, No. 14, pp. 1209-1211, Jul. 15, 2012.
Guo et al., "High-sensitivity, high-frequency extrinsic Fabry-Perot interferometric fiber-tip sensor based on a thin silver diaphragm", Optics Letters, vol. 37, No. 9, pp. 1505-1507, May 1, 2012.
Hatta et al., "SMS Fibre Structure for Temperature Measurement Using a Simple Intensity-Based Interrogation System", Electronics Letters, vol. 45, No. 21, p. 1069, Oct. 8, 2009.
Hou, Ocean Sensing and Monitoring, Chapter 1: Oceanography Overview (SPIE Press, 2013).
Hou, Ocean Sensing and Monitoring, Chapter 2: Basic Optical Properties of the Ocean (SPIE Press, 2013).
Hou, Ocean Sensing and Monitoring, Chapter 3: Underwater Sensing: Diver Visability (SPIE Press, 2013).
Hou et al, "A novel, high-resolution, high-speed, fiber-optic temperature sensor for oceanographic applications, Current, Waves and Turbulence Measurement (CWTM)," 2015 IEEE/OES Eleventh, 1-4.
Hou et al., "Optical turbulence on underwater image degradation in natural environments", Applied Optics, vol. 51, No. 14, pp. 2678-2686, May 10, 2012.
Islam et al., "Chronology of Fabry-Perot Interferometer Fiber-Optic Sensors and Their Applications: A Review", Sensors, vol. 14, pp. 7451-7488, 2014.
Kajanto et al., "A silicon-based fibre-optic temperature sensor", J. Phys. E: Sci. Instrum. vol. 21, pp. 652-656, 1988.
Khaliq et al., Enhanced sensitivity fibre optic long period grating temperature sensor, Measurement Science and Technology, vol. 13, pp. 792-795, Apr. 18, 2002.
Komma et al., "Thermo-optic coefficient of silicon at 1550 nm and cryogenic temperatures", Appl. Phys. Letters, vol. 101, Apr. 19, 2005, 2012.
Lee et al., Interferometric Fiber Optic Sensors, Sensors, vol. 12, pp. 2467-2486, Feb. 23, 2012.
Li, "Refractive index of silicon and germanium and its wavelength and temperature derivatives", J. Phys. Chem. Ret Data, vol. 9, No. 3, pp. 561-658, 1980.
Liu et al., "A miniature fiber-optic sensor for high-resolution and high-speed temperature sensing in ocean environment", Ocean Sensing and Monitoring VII, edited by Hou et al., Proc. of SPIE vol. 9459, 2015.
Liu et al., "Fast-response fiber-optic anemometer with temperature self-compensation", Optics Express, vol. 23, No. 10, pp. 13562-13570, May 18, 2015.
Liu et al., "Influence of fiber bending on wavelength demodulation of fiber-optic Fabry-Perot interferometric sensors", Optics Express, vol. 24, No. 23, pp. 26732-26744, Nov. 14, 2016.
Liu et al., "High-resolution, large dynamic range fiber-optic thermometer with cascaded Fabry-Perot cavities", Optics Letters, vol. 41, No. 21, pp. 5134-5137, Nov. 1, 2016.
Liu et al., "A fiber-optic water flow sensor based on laser-heated silicon Fabry-Perot cavity", Fiber Optic Sensors and Applications XIII, edited by Udd et al., Proc. of SPIE, vol. 9852, 2016.
Liu et al., "Fiber-optic gas pressure sensing with a laser-heated silicon-based Fabry-Perot interferometer", Optics Letters, vol. 40, No. 11, pp. 2461-2464, Jun. 1, 2015.
Liu et al., "Fiber-optic anemometer based on silicon Fabry-Perot interferometer", Fiber Optic Sensors and Applications XII, edited by Udd et al., Proc. of SPIE, vol. 9480, 2015.
Liu et al., "Optical fiber vector flow sensor based on a silicon Fabry-Perot interferometer array", Optics Letters, vol. 41, No. 20, pp. 4629-4632, Oct. 15, 2016.
Ozisik, "Heat Transfer: A Basic Approach", Chapter 8, McGraw-Hill, 1985.
Ozisik, "Heat Transfer: A Basic Approach", Chapter 9, McGraw-Hill, 1985.
Pinet, "Fabry-Perot Fiber-Optic Sensors for Physical Parameters Measurement in Challenging Conditions", Journal of Sensors, 720980, 2009.
Qu et al., "Heat transfer for water flow in trapezoidal silicon microchannels", International Journal of Heat and Mass Transfer, vol. 43, pp. 3925-3936, 2000.
Ran et al., "Laser-micromachined Fabry-Perot optical fiber tip sensor for high-resolution temperature-independent measurement of refractive index", Optics Express, vol. 16, No. 3, pp. 2252-2263, Feb. 4, 2008.
Rao, "In-fibre Bragg grating sensors", Mea. Sci. Technol., vol. 8, pp. 355-375, 1997.

* cited by examiner

FIBER OPTIC BOLOMETER

CROSS-REFERENCE TO RELATED APPLICATIONS

The present application claims the benefit under 35 U.S.C. § 119(e) of U.S. Provisional Application Ser. No. 62/347,148, filed Jun. 8, 2016, and titled "FIBER OPTIC BOLOMETER." U.S. Provisional Application Ser. No. 62/347,148 is herein incorporated by reference in its entirety.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

BACKGROUND

An optical fiber can include a flexible, transparent fiber made of extruded glass (silica) or plastic. Light can be transmitted between two ends of the optical fiber, which may be used in fiber-optic communications. A fiber optic sensor uses an optical fiber either as the sensing element (e.g., an intrinsic sensor) or as a means of relaying signals from a remote sensor to electronics that process a signal within the optical fiber (e.g., an extrinsic sensor). Fiber-optic sensors, such as intrinsic sensors, utilize optical fibers to measure temperature, strain, pressure, and/or other characteristics associated with the optical fiber.

SUMMARY

A fiber optic bolometer device is described herein. In an implementation, a fiber optic bolometer device includes an optical fiber and a silicon layer that comprises a Fabry-Pérot interferometer. The silicon layer includes a first surface and a second surface. The fiber optic bolometer device includes a reflective dielectric film disposed over the first surface of the silicon layer where the reflective dielectric film is adjacent to an end face of the optical fiber. The fiber optic bolometer device also includes an absorptive coating disposed over the second surface of the silicon layer (e.g., the surface distal to the end face of the optical fiber). This absorptive coating may also serve as a mirror of the Fabry Pérot interferometer.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

Figure 1A:
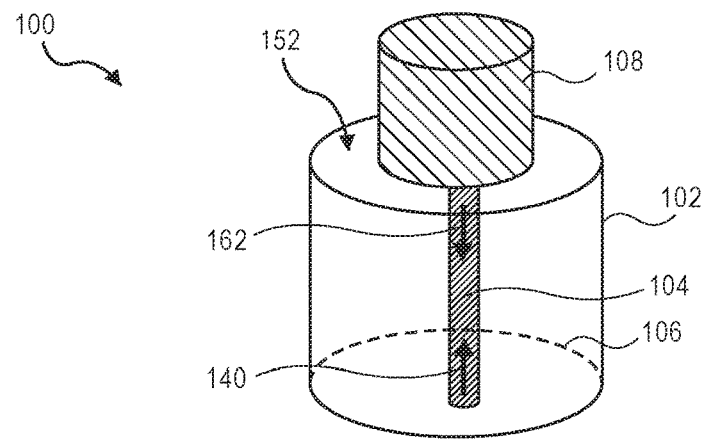
FIG. 1A is an isometric view illustrating an embodiment of a fiber optic sensor that includes a silicon layer disposed on an end face of an optical fiber, in accordance with an example implementation of the present disclosure.
Figure 1B:
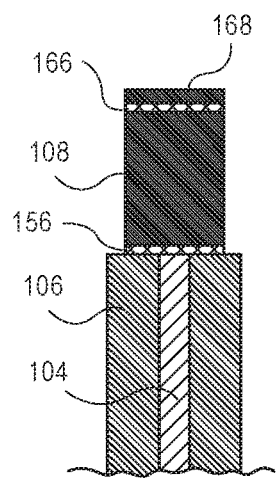
FIG. 1B is a partial side elevation cross section view illustrating an embodiment of a fiber optic sensor that includes multiple cascaded silicon layers disposed on an end face of an optical fiber, in accordance with an example implementation of the present disclosure.
Figure 1C:
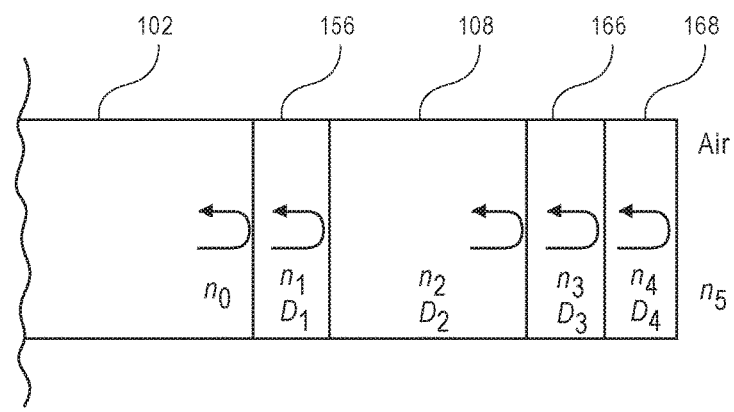
FIG. 1C is a partial side elevation cross section view illustrating an embodiment of a fiber optic sensor that includes multiple cascaded silicon layers disposed on an end face of an optical fiber, in accordance with an example implementation of the present disclosure.
Figure 1D:
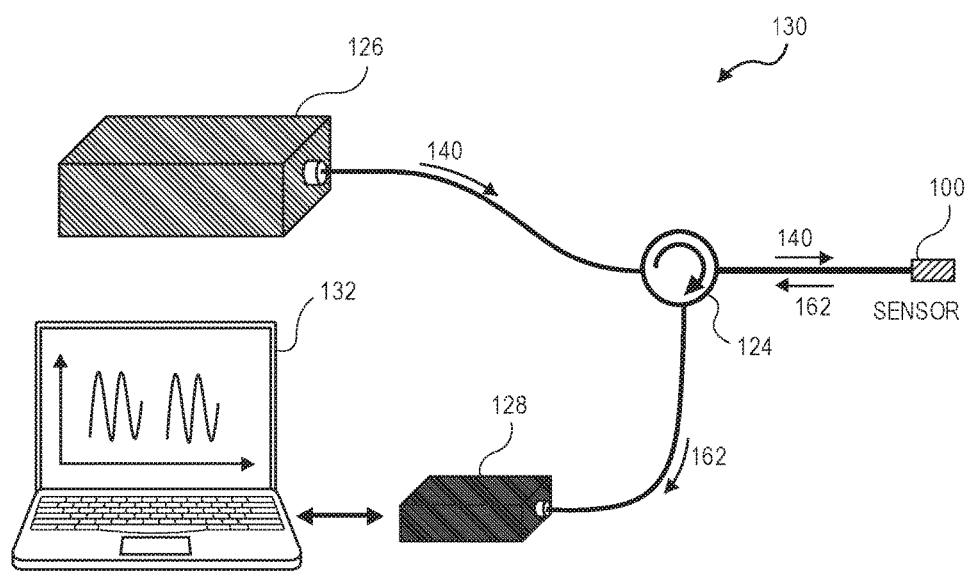
FIG. 1D is an environmental view illustrating an embodiment of a fiber optic sensing system that includes a fiber optic sensor with a silicon layer disposed on an end face of an optical fiber, in accordance with an example implementation of the present disclosure.
Figure 1E:
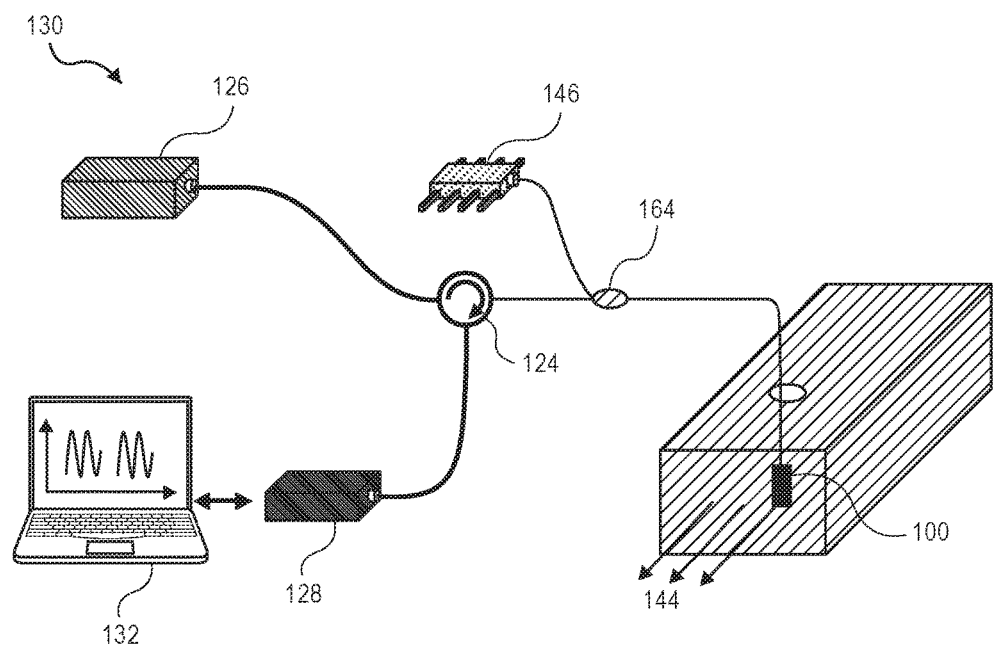
FIG. 1E is an environmental view illustrating an embodiment of a fiber optic sensing system that includes a fiber optic sensor with a silicon layer disposed on an end face of an optical fiber, in accordance with an example implementation of the present disclosure.
Figure 1F:
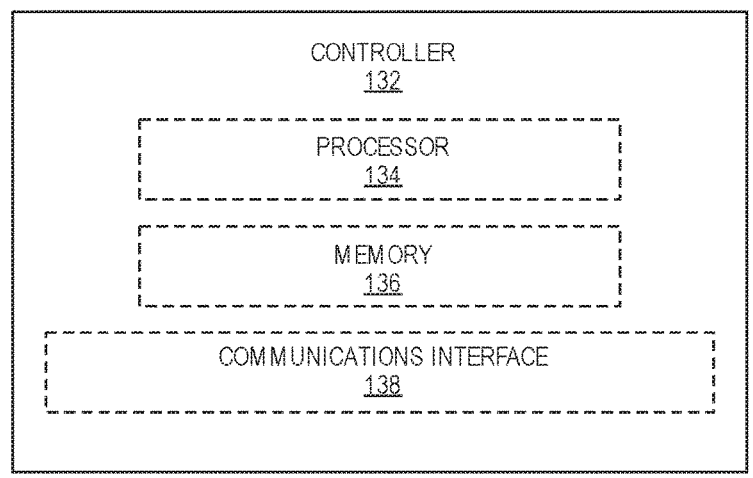
FIG. 1F is an environmental view illustrating an embodiment of a controller used in a fiber optic sensing system, in accordance with an example implementation of the present disclosure.
Figure 1G:
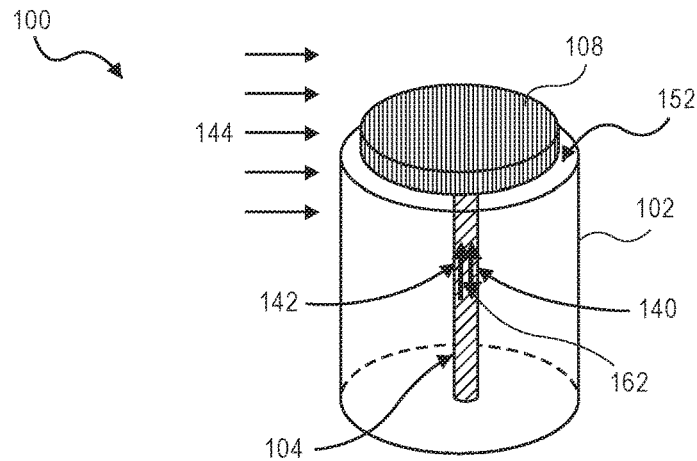
FIG. 1G is an isometric view illustrating an embodiment of a fiber optic sensor that includes a silicon layer disposed on an end face of an optical fiber, in accordance with an example implementation of the present disclosure.
Figure 1H:
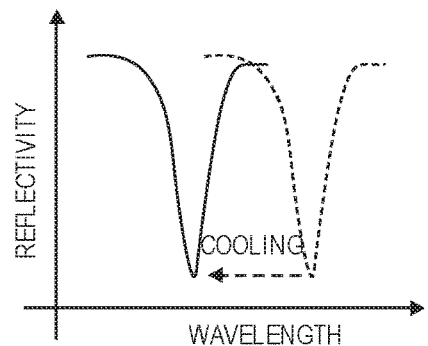
FIG. 1H is a graphical depiction illustrating a wavelength shift that represents a temperature change using a fiber optic sensor that includes a silicon layer disposed on an end face of an optical fiber, in accordance with an example implementation of the present disclosure.
Figure 1I:
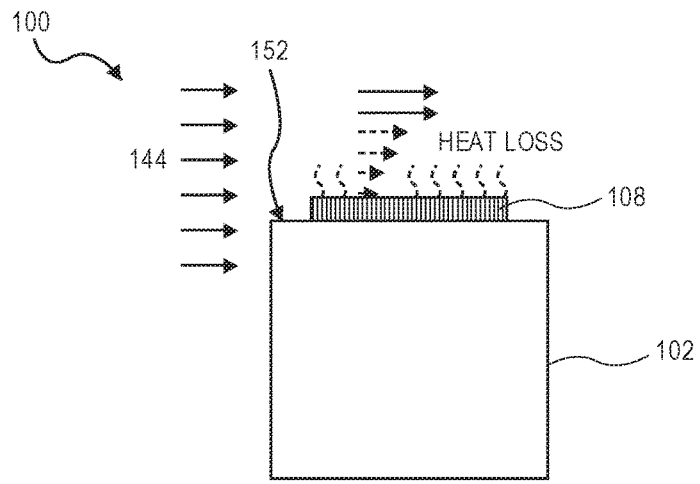
FIG. 1I is a side elevation cross sectional view illustrating an embodiment of a fiber optic sensor that includes a silicon layer disposed on an end face of an optical fiber, in accordance with an example implementation of the present disclosure.
Figure 1J:
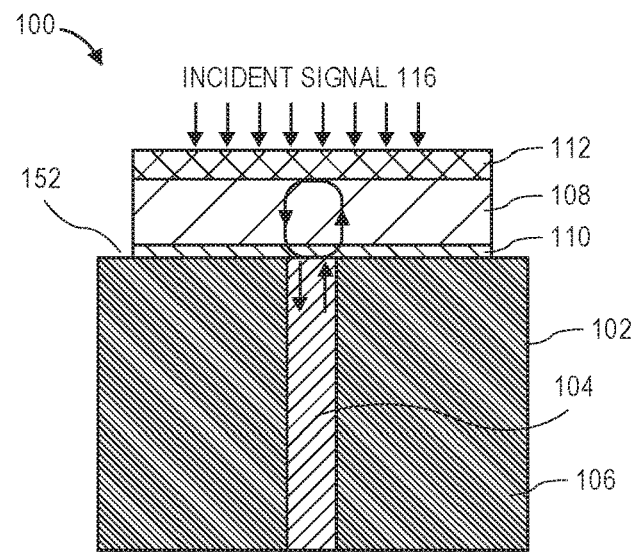

FIG. 1J is a side elevation cross sectional view illustrating an embodiment of a fiber optic bolometer sensor that includes a silicon layer disposed on an end face of an optical fiber where the silicon layer includes a reflective dielectric film disposed over a first surface and an absorptive and reflective coating disposed over a second surface in accordance with an example implementation of the present disclosure.

Figure 1K:
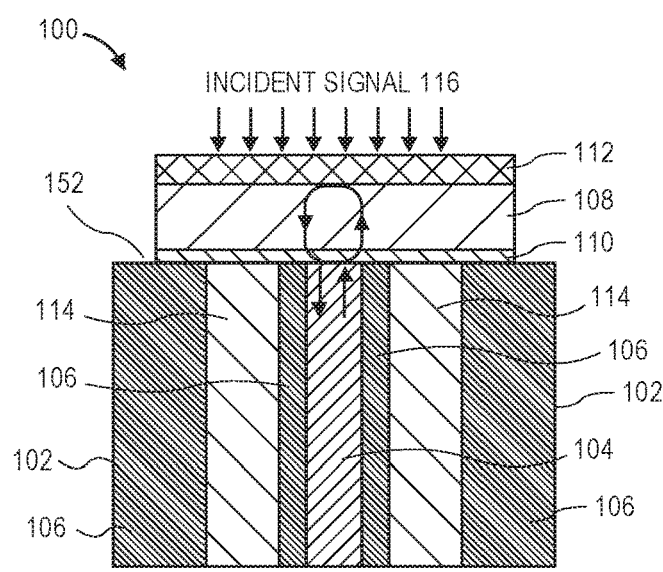

FIG. 1K is a side elevation cross sectional view illustrating an embodiment of fiber optic bolometer sensor in accordance with an example implementation of the present disclosure.

Figure 1L:
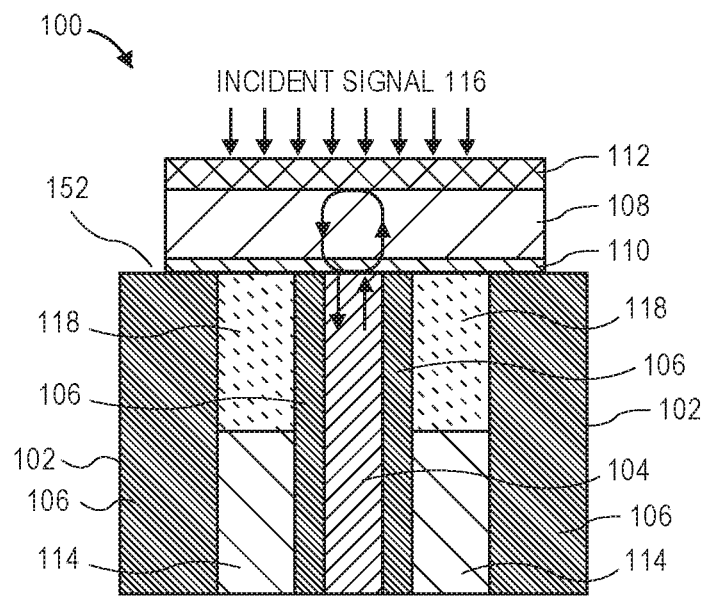

FIG. 1L is a side elevation cross sectional view illustrating an embodiment of fiber optic bolometer sensor in accordance with an example implementation of the present disclosure.

Figure 1M:
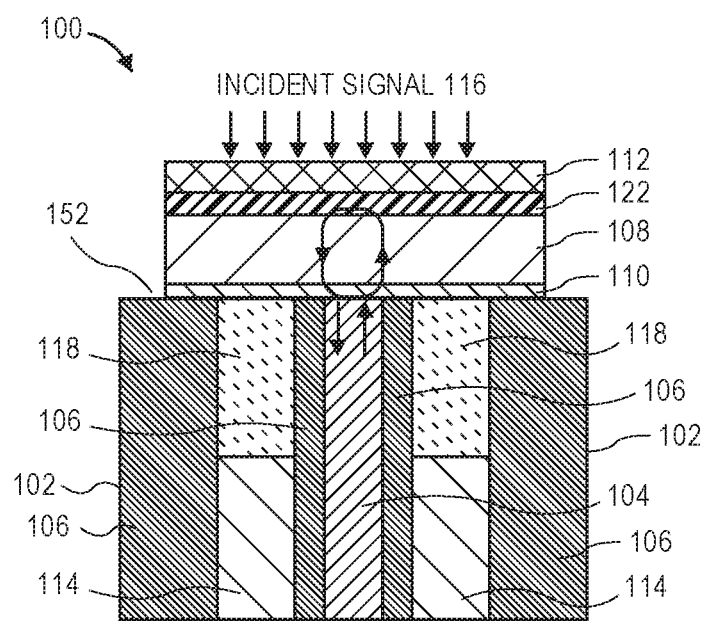

FIG. 1M is a side elevation cross sectional view illustrating an embodiment of fiber optic bolometer sensor in accordance with an example implementation of the present disclosure.

Figure 1N:
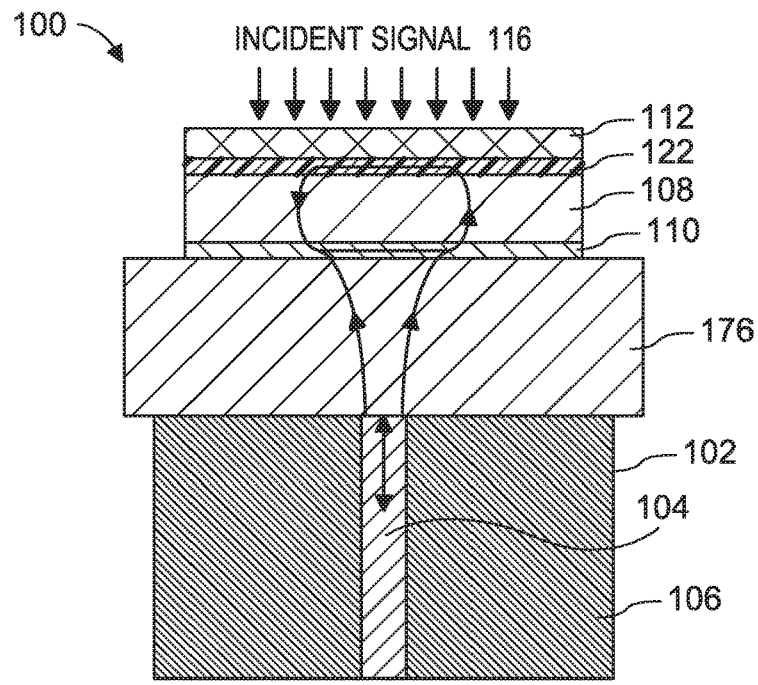

FIG. 1N is a side elevation cross sectional view illustrating an embodiment of fiber optic bolometer sensor in accordance with an example implementation of the present disclosure.

Figure 1O:
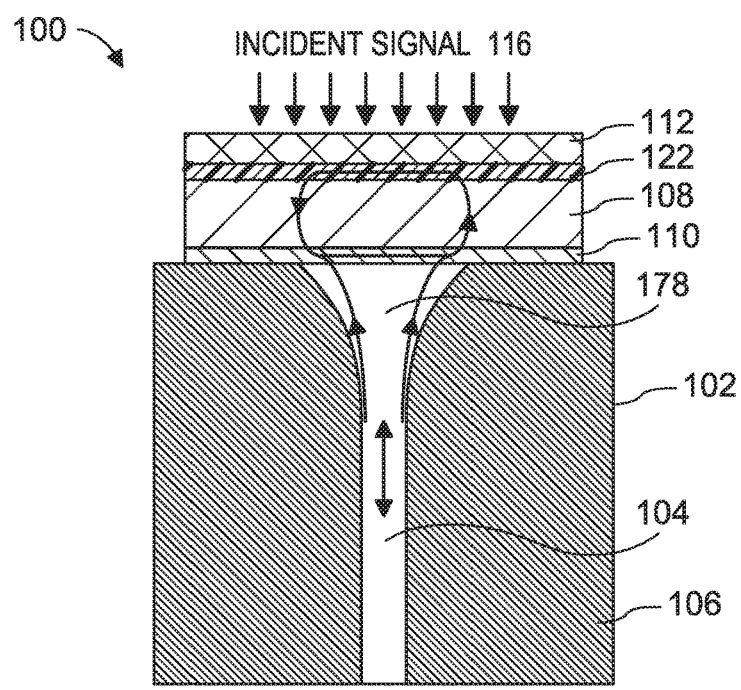

FIG. 1O is a side elevation cross sectional view illustrating an embodiment of fiber optic bolometer sensor in accordance with an example implementation of the present disclosure.

Figure 2A:
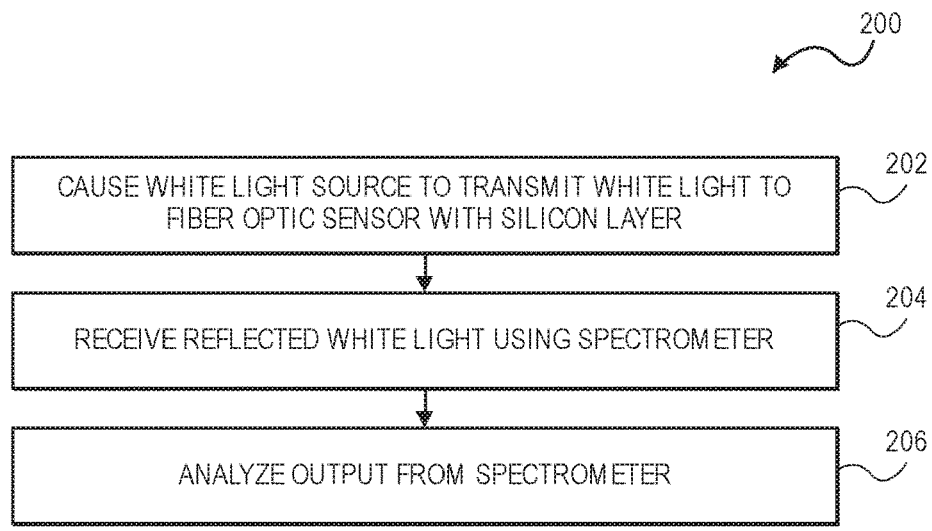

FIG. 2A is a flow diagram illustrating an example process for using a fiber optic sensor that includes a silicon layer disposed on an end face of an optical fiber, such as the fiber optic sensor illustrated in FIGS. 1A through 1G.

Figure 2B:
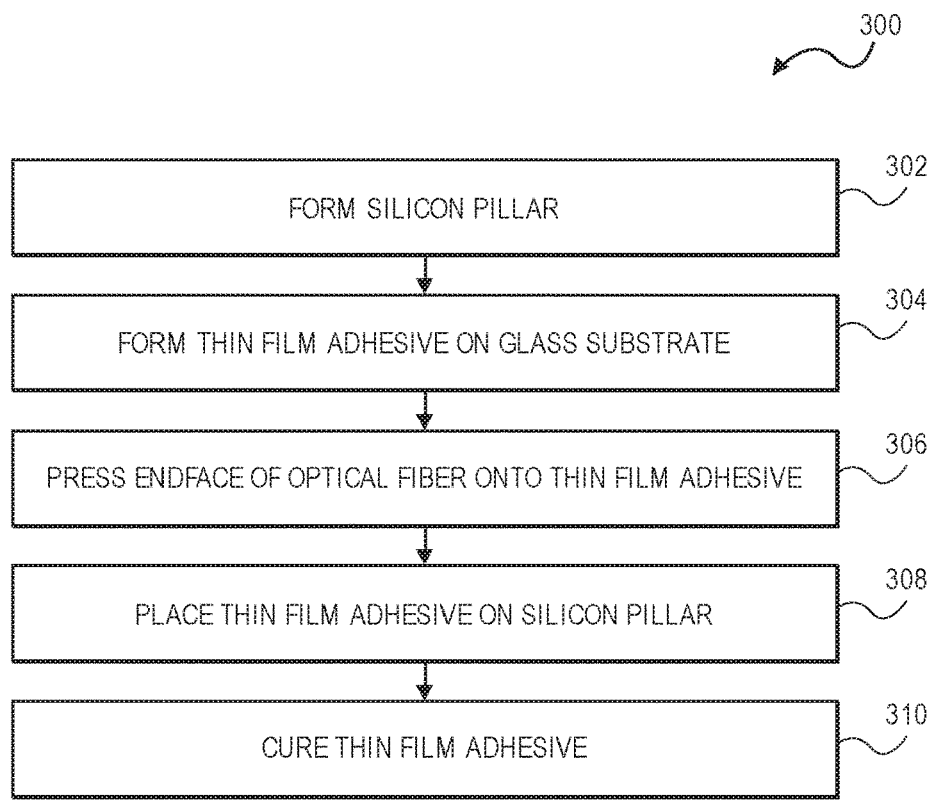

FIG. 2B is a flow diagram illustrating an example process for fabricating a fiber optic sensor that includes a silicon layer disposed on an end face of an optical fiber, such as the fiber optic sensor illustrated in FIGS. 1A through 1G.

Figure 2C:
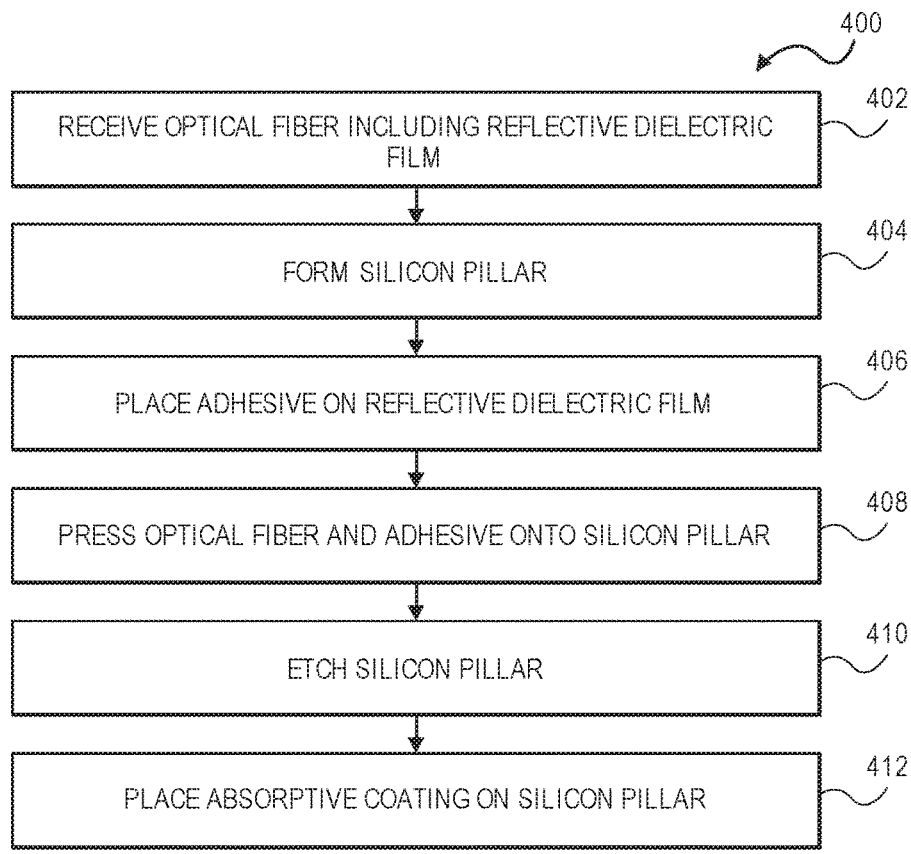

FIG. 2C is a flow diagram illustrating an example process for fabricating a fiber optic bolometer device that includes a silicon layer disposed on an end face of an optical fiber, such as the fiber optic sensor illustrated in FIGS. 1J through 1M.

Figure 2D:
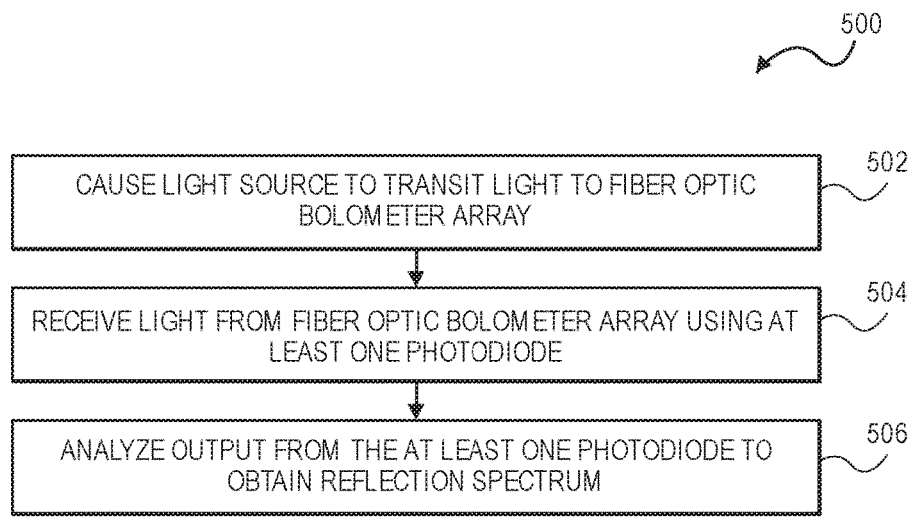

FIG. 2D is a flow diagram illustrating an example process for demodulating an array of fiber optic bolometer devices that includes a silicon layer disposed on an end face of each optical fiber, such as the fiber optic bolometer device illustrated in FIGS. 1J through 1M.

Figure 3A:
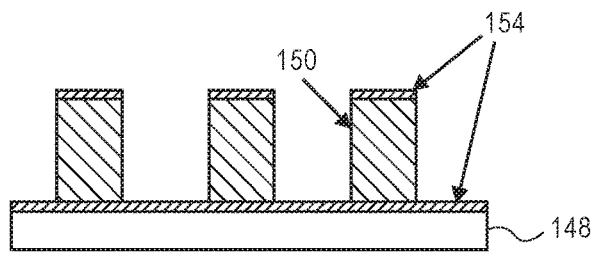

FIG. 3A is a diagrammatic partial cross-sectional side elevation view illustrating the fabrication of a fiber optic sensor that includes a silicon layer disposed on an end face of an optical fiber, such as the fiber optic sensor illustrated in FIGS. 1A through 1G, in accordance with the process shown in FIG. 2B.

Figure 3B:
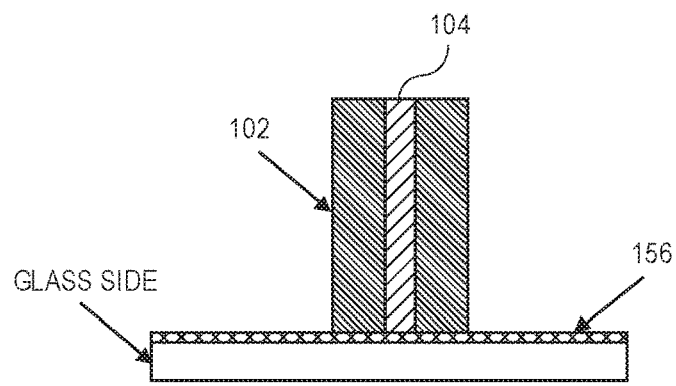

FIG. 3B is a diagrammatic partial cross-sectional side elevation view illustrating the fabrication of a fiber optic sensor that includes a silicon layer disposed on an end face of an optical fiber, such as the fiber optic sensor illustrated in FIGS. 1A through 1G, in accordance with the process shown in FIG. 2B.

Figure 3C:
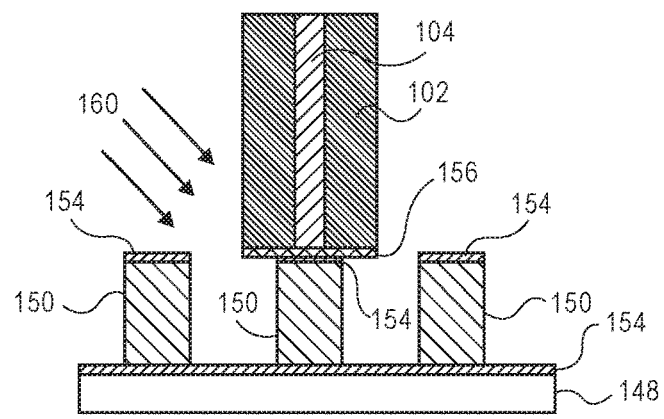

FIG. 3C is a diagrammatic partial cross-sectional side elevation view illustrating the fabrication of a fiber optic sensor that includes a silicon layer disposed on an end face of an optical fiber, such as the fiber optic sensor illustrated in FIGS. 1A through 1G, in accordance with the process shown in FIG. 2B.

Figure 3D:
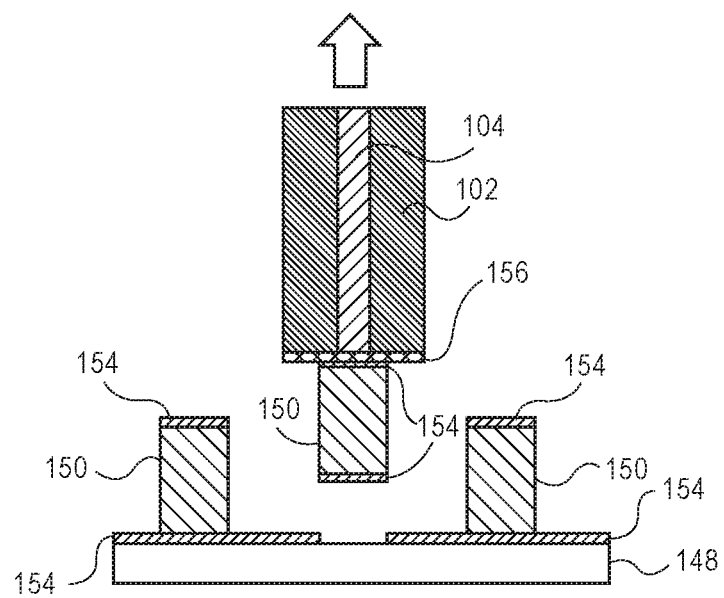

FIG. 3D is a diagrammatic partial cross-sectional side elevation view illustrating the fabrication of a fiber optic sensor that includes a silicon layer disposed on an end face of an optical fiber, such as the fiber optic sensor illustrated in FIGS. 1A through 1G, in accordance with the process shown in FIG. 2B.

Figure 3E:
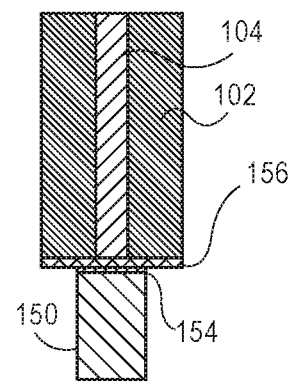

FIG. 3E is a diagrammatic partial cross-sectional side elevation view illustrating the fabrication of a fiber optic sensor that includes a silicon layer disposed on an end face of an optical fiber, such as the fiber optic sensor illustrated in FIGS. 1A through 1G, in accordance with the process shown in FIG. 2B.

Figure 4A:
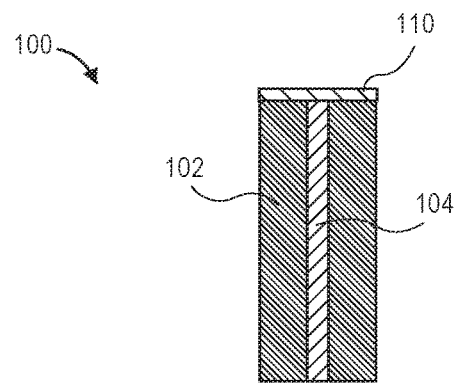

FIG. 4A is a diagrammatic partial cross-sectional side elevation view illustrating the fabrication of a fiber optic bolometer device that includes a silicon layer disposed on an end face of an optical fiber, such as the fiber optic bolometer device illustrated in FIGS. 1J through 1M, in accordance with the process shown in FIG. 2C.

Figure 4B:
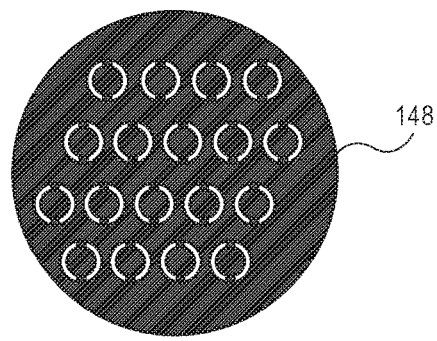

FIG. 4B is a top plan view illustrating the fabrication of a fiber optic bolometer device that includes a silicon layer disposed on an end face of an optical fiber, such as the fiber optic bolometer device illustrated in FIGS. 1J through 1M, in accordance with the process shown in FIG. 2C.

Figure 4C:
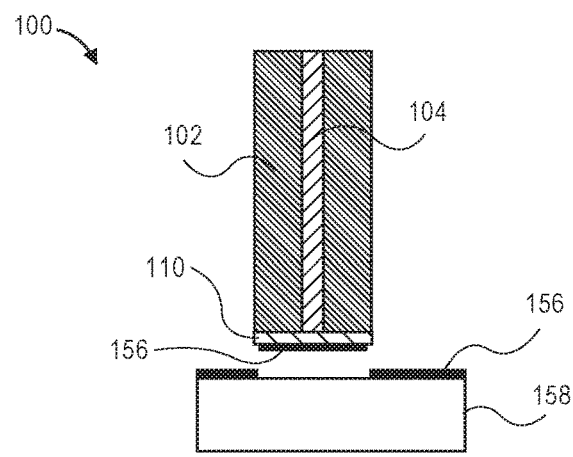

FIG. 4C is a diagrammatic partial cross-sectional side elevation view illustrating the fabrication of a fiber optic bolometer device that includes a silicon layer disposed on an end face of an optical fiber, such as the fiber optic bolometer device illustrated in FIGS. 1J through 1M, in accordance with the process shown in FIG. 2C.

Figure 4D:
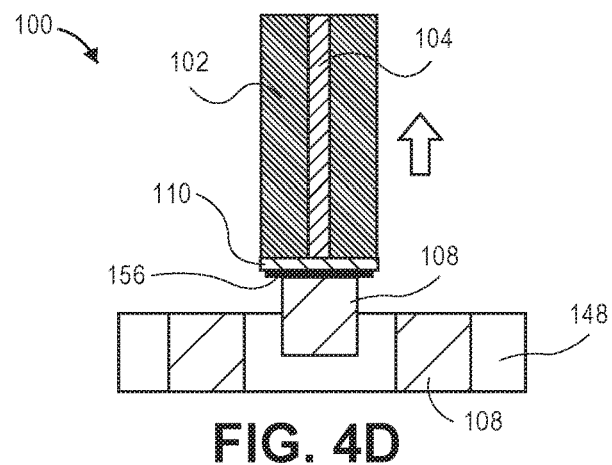

FIG. 4D is a diagrammatic partial cross-sectional side elevation view illustrating the fabrication of a fiber optic bolometer device that includes a silicon layer disposed on an end face of an optical fiber, such as the fiber optic bolometer device illustrated in FIGS. 1J through 1M, in accordance with the process shown in FIG. 2C.

Figure 4E:
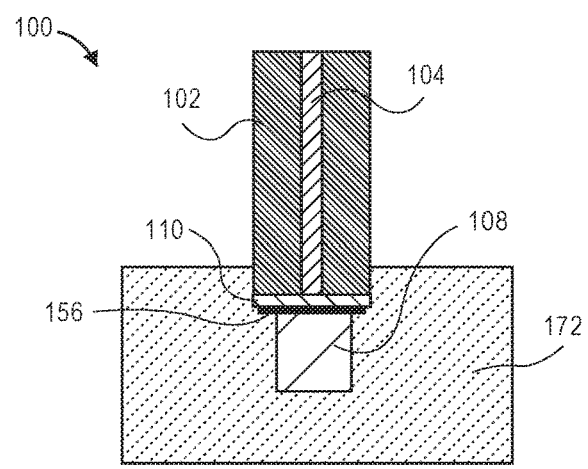

FIG. 4E is a diagrammatic partial cross-sectional side elevation view illustrating the fabrication of a fiber optic bolometer device that includes a silicon layer disposed on an end face of an optical fiber, such as the fiber optic bolometer device illustrated in FIGS. 1J through 1M, in accordance with the process shown in FIG. 2C.

Figure 4F:
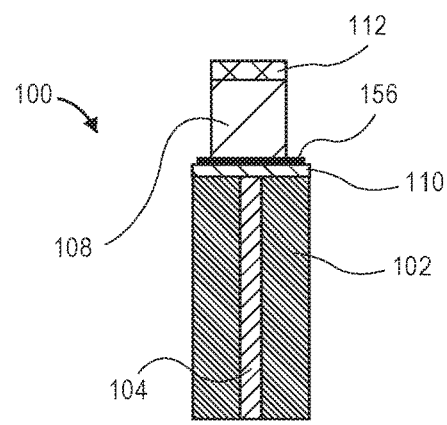

FIG. 4F is a diagrammatic partial cross-sectional side elevation view illustrating the fabrication of a fiber optic bolometer device that includes a silicon layer disposed on an end face of an optical fiber, such as the fiber optic bolometer device illustrated in FIGS. 1J through 1M, in accordance with the process shown in FIG. 2C.

Figure 5:
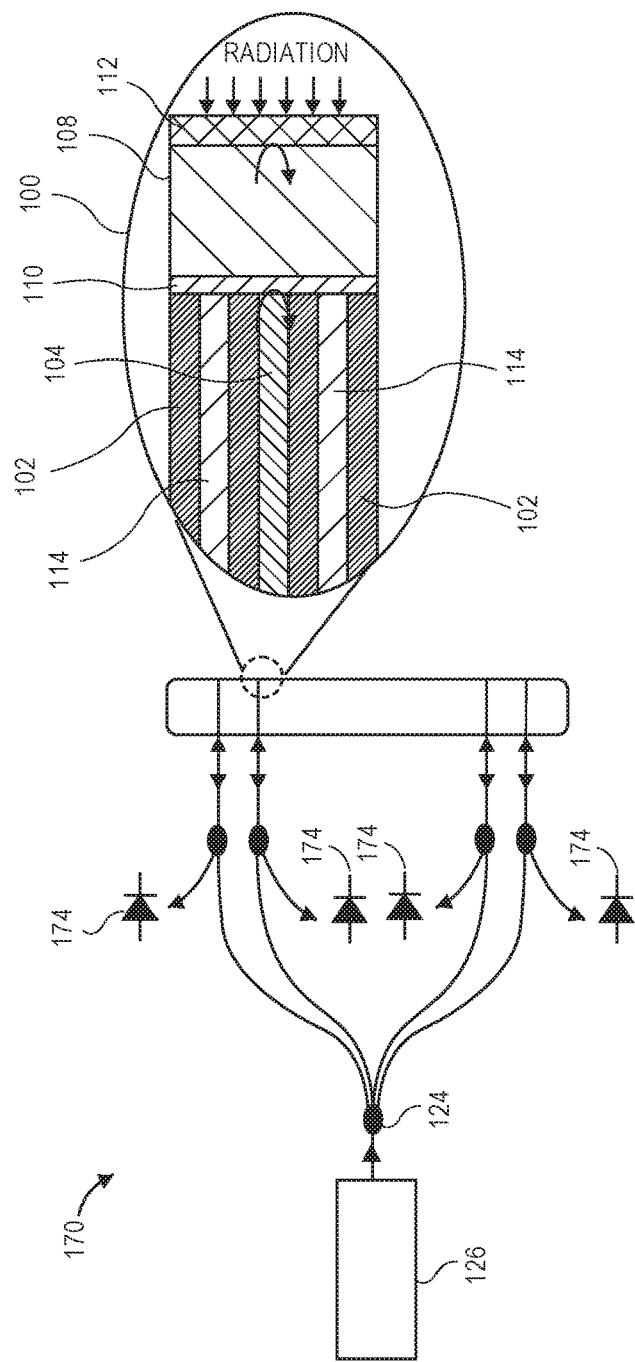

FIG. 5 is an environmental view illustrating an embodiment of a fiber optic bolometer device array that includes multiple fiber optic bolometer devices with a silicon layer and an absorptive layer disposed on an end face of an optical fiber, in accordance with an example implementation of the present disclosure.

DETAILED DESCRIPTION

Measurement of speed of gas or liquid flow is of great practical importance in a variety of industries, such as food inspection, pharmacy, oil/gas exploration, environmental, high-voltage power systems, chemical plants, and oceanography research. Owing to their many unique advantages, such as small size, light weight, immunity to electromagnetic interference, remote sensing capability, harsh environment tolerance, and capability for distributed or quasi-distributed measurement fiber-optic sensors, such as temperature sensors, flowmeters, or anemometers, have proven to be attractive alternatives to their traditional mechanical or electromagnetic counterparts.

In addition to sensitivity and temperature range, two important sensor parameters include temperature resolution and speed (or response time). Temperature resolution, defined as the minimum detectable temperature changes, is determined by both the sensor sensitivity (defined as the sensor output from a given temperature change) and the noise of the sensor system, while the response time is mostly limited by the time constant of the heat transfer process between the sensing element and the surrounding environment. The sensing element of many fiber-optic temperature sensors is part of the fiber itself, which is made of fused silica. The temperature resolution and the speed are limited by the relatively low thermo-optic coefficient (TOC) and thermal diffusivity of the glass material that lead, respectively, to a reduced sensor sensitivity and increased time for the temperature of the sensing element to reach equilibrium with the surrounding environment. For example, it is well-known that a fiber Bragg grating (FBG), whose reflection spectrum features a single reflection peak, exhibit a temperature sensitivity of about 10 pm/° C. A fiber modal interferometer based on a single mode-multimode-single mode fiber structure has been reported to have a temperature resolution of 0.2° C. Many all-silica-fiber-based temperature sensors possess relatively low sensitivity and relatively low temperature resolution. As to the response time, a package of a FBG with a copper tube encapsulation can greatly reduce the response time of the sensor from several seconds to 48.6 milliseconds (ms) in water. A response time of 16 ms in air has been demonstrated for a microfiber coupler tip temperature sensor.

Compared to fused silica, crystalline silicon is a much more desirable sensor material for high-resolution and high-speed temperature sensing. Silicon is highly transparent over the infrared wavelength and has a TOC approximately 10 times larger than that of fused silica used for the sensing element for most fiber-optic sensors, resulting in potentially much higher temperature sensitivity. In addition, a silicon-based temperature sensor also has high speed because of the large thermal diffusivity of silicon, which is comparable to many metals (e.g., aluminum and gold) and is more than 60 times larger than fused silica. However, the use of silicon as a temperature sensing element has not been utilized on a large scale for high-resolution and high-speed temperature sensing. The dependence of the absorption of a silicon film on temperature for temperature sensing and the sensor has shown a relatively low temperature resolution of ±0.12° C. and a long response time on the order of 1 second (s). A simpler structure with a thin silicon film (thickness <1 µm) deposited directly on the fiber end through electron-beam evaporation has shown a temperature resolution of only 3° C. In this case, radio-frequency sputtering was applied to simplify the deposition process, and the resolution was mainly limited by the small thickness of the silicon film that led to broad spectral fringes. Instead of silicon film, a silicon micro-waveguide patterned on a micro-electro-mechanical system (MEMS) was developed as temperature sensor, and due to the increased length of the Si sensing element, the temperature resolution was improved to 0.064° C. However, it is a challenge to integrate the fiber and the MEMS into a single sensor device, and the large size of previous sensing elements also limit their temperature measurement speed.

Accordingly, a fiber optic sensor, a process for utilizing a fiber optic sensor, and a process for fabricating a fiber optic sensor are described, where a double-side-polished silicon pillar is attached to an optical fiber tip and forms a Fabry-Pérot (FP) cavity and a sensor head. As described herein, the Fabry-Pérot (FP) cavity may comprise a Fabry-Pérot (FP) cavity bolometer (e.g., a fiber-optic bolometer device or a fiber-optic bolometer sensor). The bolometer is configured to measure the power of incident electromagnetic radiation via the heating of a material with a temperature-dependent electrical resistance.

In an implementation, a fiber optic bolometer device includes an optical fiber and a silicon layer that comprises a Fabry-Pérot interferometer. The silicon layer includes a first surface and a second surface. The fiber optic bolometer device includes a reflective dielectric film disposed over the first surface of the silicon layer where the reflective dielectric film is adjacent to an end face of the optical fiber. The fiber optic bolometer device also includes an absorptive coating disposed over the second surface of the silicon layer (e.g., the surface distal to the end face of the optical fiber).

Example Implementations

FIGS. 1A through 1N illustrate a fiber optic sensor 100 (fiber optic bolometer device 100) and fiber optic sensing system 130 in accordance with an example implementation of the present disclosure. The fiber optic sensor 100 can include an optical fiber 102 configured to be coupled to a light source 126 and a high speed spectrometer 128. The fiber optic sensor 100 and fiber optic sensing system 130 may be utilized as a temperature sensor in determining temperature in gas and liquid.

In implementations, the optical fiber 102 can include a flexible, transparent fiber core 104 made of extruded glass (e.g., silica) or a polymer. The optical fiber 102 can be configured to transmit light between the two ends of the optical fiber 102. In some instances, the optical fiber 102 may be immune to electromagnetic interference.

The optical fiber 102 can include the core 104 and/or a cladding 106. The core 104 may include a fiber of glass and/or plastic that extends along the length of the optical fiber 102. The core 104 may be surrounded by a cladding 106, which may include a material with a lower index of refraction than the core 104. In embodiments, the cladding 106 may include a cladding of a different glass and/or plastic, a buffer layer, and/or a jacket.

In some instances, the polarization of the light in regular single-mode optical fibers may not be stable. Mechanical or thermal perturbations to the optical fiber 102 may change the polarization. Due to the potential birefringence of the silicon layer 108 and/or the reflective dielectric thin film 110, the optical length of the FPI may be dependent on the light polarization. The changes of the polarization may lead to the change of the optical signal, which may not be distinguished from the change from the radiation. To eliminate the issues from the birefringence of the FPI, some embodiments of the fiber optic sensor 100 may include an optic fiber 102 comprising polarization-maintaining fibers (PMFs), where the polarization of the light beam in the fiber is maintained during the light propagation in the fiber.

As illustrated in FIG. 1A, the fiber optic sensor 100 can include a silicon layer 108 disposed on an end face 152 of the optical fiber 102 (e.g., a cleaved portion of the optical fiber 102), which forms a sensor head. In implementations, the silicon layer 108 can include a silicon pillar and/or a silicon-based film. In a specific embodiment, the silicon layer 108 includes a double-sided polished silicon pillar. In another specific embodiment, the silicon layer 108 can include a piece of a silicon wafer bonded to the end face 152. The silicon layer 108 may include various diameters and/or lengths. For example, the silicon layer 108 can include a silicon pillar with a diameter between about 80 µm to 100 µm with a length of about 200 pm. In another example, the silicon layer 108 may include a piece of silicon that is approximately 10 µm thick. In yet another example, the silicon layer 108 can include a piece of silicon that is approximately 200 µm thick. It is contemplated that the silicon layer 108 may include other diameters and/or lengths. The silicon layer 108 diameter is generally less than the diameter of the optical fiber 102, which leads to a fast temperature response. The silicon in the silicon layer 108 is highly transparent over the infrared wavelength and has a TOC approximately 10 times larger than that of the silica used in the optical fiber 102 for most fiber-optic sensors, resulting in potentially much higher temperature sensitivity. In addition, the fiber optic sensor 100 also has high speed because of the large thermal diffusivity of silicon, which is comparable to many metals (e.g., aluminum and gold) and more than 60 times larger than fused silica. In other implementations, the silicon layer 108 may be replaced with other materials that have large thermal diffusivity and high thermo-optic and thermal expansion coefficients. Further, it is contemplated that the silicon layer 108 can include other configurations, such as a cuboid configuration.

As illustrated in FIGS. 1B and 1C, the fiber optic sensor 100 may include cascaded Fabry-Pérot cavities. In these implementations, the fiber optic sensor 100 can include an adhesive 156 disposed on an end face 152 of the optical fiber 102, a silicon layer 108 disposed on the adhesive 156, a second adhesive 166 disposed on the silicon layer 108, and a second silicon layer 168 disposed on the second adhesive 166. The silicon layer 108 and the second silicon layer 168 include the same material so that each has the same responsivity to temperature. In such a way, the large free spectrum range (FSR) of the envelope originating from the second silicon layer 168 (the second Fabry-Pérot interferometer) provides large dynamic range, while the recognized dense fringes with small FSR stemming from the silicon layer 108 (the first Fabry-Pérot interferometer) offers high resolution due to the narrow fringes. The adhesive 156 and/or the second adhesive 166 can include materials suitable to bond the optical fiber 102, the silicon layer 108, and/or the second silicon layer 168 (e.g., a UV glue, etc.). Additionally, the adhesive 156 and/or the second adhesive 166 can be the same or similar diameter as the silicon layer 108 and/or second silicon layer 168, while the thickness of the adhesive 156 and/or the second adhesive 166 can be only a few microns (e.g., <1 μm, 2 μm, 3 μm, etc.). Because the adhesive 156 and/or the second adhesive 166 are very thin compared to the silicon layer 108 and the second silicon layer 168, they show negligible influence on the reflection spectrum of reflected light 162. In specific embodiments, the silicon layer 108 and the second silicon layer 168 can be the same or similar diameters but have different lengths (e.g., the silicon layer 108 is 200 μm in length and the second silicon layer 168 is 10 μm in length). It is contemplated that the silicon layer 108 and/or the second silicon layer 168 can include a variety of lengths and/or diameters. In FIG. 1C, $n_i$ and $D_i$ represent the refractive index and separation of the $i^{th}$ layer, respectively. These implementations provide an optical fiber thermometer based on double cascaded Fabry-Pérot interferometers both made from the same material of silicon but with vastly different cavity lengths to achieve both large dynamic and high resolution.

In implementations, the fiber optic sensor 100 defines and includes a Fabry-Pérot (FP) cavity. A Fabry-Pérot cavity (or Fabry-Pérot interferometer) can include a cavity formed by the optical fiber 102 and the silicon layer 108 disposed on the end face 152 of the optical fiber 102. Due to the thermo-optic effect, temperature variations change the optical thickness of the FP cavity and consequently cause spectral shifts in its reflection spectrum.

As illustrated in FIG. 1D, the fiber optic sensing system 130 can include the fiber optic sensor 100, a light source 126, a circulator 124, a spectrometer 128, and a controller 132. In some implementations, the fiber optic sensing system 130 may include a heating light source 146.

In implementations, the light source 126 (e.g., a broad band source) transmits light to the circulator 124 and the fiber optic sensor 100. In one specific embodiment, light source 126 includes a wavelength swept laser, such as a high-speed, narrow-linewidth, and wavelength-swept laser. In another specific embodiment, light source 126 includes a laser diode. In yet another specific embodiment, light source 126 includes a white light source (e.g., 1550 nm). It is contemplated that the light source 126 can include other types of light sources. In implementations, the light source 126 is optically coupled to the optical fiber 102, which is optically coupled to a circulator 124. Additionally, the light source 126 can be coupled to and controlled using controller 132.

As illustrated in FIG. 1E, the fiber optic sensing system 130 may include a heating light source 146 configured to provide heating light 142. In these embodiments, the heating light source 146 can include a light source, such as a red laser diode, that is optically coupled to the optical fiber 102 using a coupler 164. In one specific instance, the heating light source 146 can include a 635 nm diode laser. The heating light source 146 may include other light sources that provide light, which can be absorbed by the fiber optic sensor 100 and/or the silicon layer 108. Additionally, the heating light source 146 can be controlled using controller 132.

A circulator 124 can include a fiber-optic component used to separate optical signals in optical fiber 102. In implementations, circulator 122 can direct transmitted light 140 from light source 126 (and/or heating light 142 from heating light source 146) to fiber optic sensor 100 while directing reflected light 162 from the fiber optic sensor 100 to spectrometer 128.

The fiber optic sensing system 130 can include a spectrometer 128 coupled to the optical fiber 102 and a controller 132. In implementations, a spectrometer 128 can include a light sensor, such as a photodetector, configured to detect reflected light 162 and the associated spectra from the optical fiber 102 and fiber optic sensor 100. In a specific embodiment, the spectrometer 128 may include a high-speed photodetector (e.g., the high speed spectrometer from Ibsen Photonics, I-MON 256 USB, Denmark). Additionally, the spectrometer 128 can be coupled to and controlled using controller 132.

As reflected light 162 is received and/or detected by spectrometer 128, a shift in wavelength is detected when temperature changes at the silicon layer 108. The wavelength of the $N^{th}$ fringe peak, $\lambda_N$, of the reflection spectrum is given as $$\left(N + \frac{1}{2}\right)\lambda_N = 2nL \qquad \text{Eq. 1}$$

where n and L are, respectively, the RI and cavity length of the FP cavity. Both n and L are dependent on temperature due to the thermo-optic effect and the thermal expansion of the silicon material. Therefore, temperature change can be measured by monitoring $\lambda_N$. From Eq. 1, the temperature sensitivity is given by $$\frac{\partial \lambda_N}{\partial T} = \lambda_N \left(\frac{1}{n}\frac{\partial n}{\partial T} + \frac{1}{L}\frac{\partial L}{\partial T}\right) \qquad \text{Eq. 2}$$

Although Eqs. 1 and 2 only depict one of the multiple peaks in the reflected spectrum from the sensor, in some cases, an average wavelength may be applied to significantly reduce the noise lever or increase the resolution. This average wavelength can be obtained from multiple peaks or valleys or both.

The sensitivity depends on the TOC and the thermo-expansion coefficient (TEC) of the sensing material. The TOC and TEC for silicon are, respectively, $1.5 \times 10^{-4}$ RIU/° C. and $2.55 \times 10^{-6}$ m/(m·° C.) at 25° C. To estimate the sensitivity, these values are applied to Eq. (2) at the peak wavelength $\lambda_N$ around 1550 nm and the RI of silicon is assumed to be 3.4. From this, the sensitivity of the temperature sensor proposed here is estimated to be 72 pm/° C. As a comparison to the all-fiber based sensor, the TOC and TEC for fused silica are, respectively, $1.28 \times 10^{-5}$ RIU/° C. and $5.5 \times 10^{-7}$ m/(m·° C.) at 25° C., both of which are much smaller than those for silicon. Assuming the RI of silica at 1550 nm is 1.5, the sensitivity of an all-fiber based sensor is about 14 pm/° C., which is more than 5 times smaller than the fiber optic sensor 100.

The high RI (about 3.4) of silicon over infrared wavelength range produces a high reflectivity at the interfaces between silicon layer 108 and the surrounding environment and between silicon layer 108 and the fiber end face 152, which facilitates to obtain a large optical power and a high fringe-visibility of the interferometric spectrum from the FP cavity for improving the sensor resolution. In addition, the high RI and the relatively long FP cavity yield a large number of fringes within the wavelength range of the spectrometer, which can be exploited to further increase the temperature resolution.

The fiber optic sensor 100 also features a short response time. Due to the high thermal diffusivity of silicon and the small size of the sensor head, the temperature within the FP cavity can quickly reach equilibrium with surroundings.

As illustrated in FIG. 1B, the fiber optic sensing system 130 can include a controller 132 that is configured to determine a shift in spectra detected by spectrometer 128 using a fiber optic sensor 100. The controller 132 can be coupled to the components of the fiber optic sensing system 130. Additionally, the controller 132 may be configured in a variety of ways. As illustrated in FIG. 1F, the controller 132 is illustrated as including a processor 134, a memory 136, and a communications interface 138. The processor 134 provides processing functionality for the fiber optic sensor 100 and may include any number of processors, microcontrollers, or other processing systems, and resident or external memory for storing data and other information accessed or generated by the fiber optic sensor 100. The processor 134 may execute one or more software programs that implement the techniques and modules described herein. The processor 134 is not limited by the materials from which it is formed or the processing mechanisms employed therein and, as such, may be implemented via semiconductor(s) and/or transistors (e.g., electronic integrated circuits (ICs)), and so forth.

The memory 136 is an example of a non-transitory computer storage device that provides storage functionality to store various data associated with the operation of the fiber optic sensor 100, such as the software program and code segments mentioned above, computer instructions, and/or other data to instruct the processor 134 and other elements of the fiber optic sensor 100 to perform the techniques described herein. Although a single memory 136 is shown, a wide variety of types and combinations of memory may be employed. The memory 136 may be integral with the processor 134, stand-alone memory, or a combination of both. The memory may include, for example, removable and non-removable memory elements such as RAM, ROM, Flash (e.g., SD Card, mini-SD card, micro-SD Card), magnetic, optical, USB memory devices, and so forth.

The communications interface 138 is operatively configured to communicate with components of the fiber optic sensor 100. For example, the communications interface 138 can be configured to transmit data for storage in the controller 132, retrieve data from storage in the controller 132, and so forth. The communications interface 138 is also communicatively coupled with the processor 134 to facilitate data transfer between components of the fiber optic sensing system 130 and the processor 134 (e.g., for communicating inputs to the processor 134 received from a device communicatively coupled with the fiber optic sensing system 130). It should be noted that while the communications interface 138 is described as a component of fiber optic sensing system 130, one or more components of the communications interface 138 can be implemented as external components communicatively coupled to the fiber optic sensing system 130 via a wired and/or wireless connection.

The fiber optic sensing system 130 can also comprise and/or connect to one or more input/output (I/O) devices (e.g., via the communications interface 138) including, but not necessarily limited to a display, a mouse, a touchpad, a keyboard, and so on.

The communications interface 138 and/or the processor 134 can be configured to communicate with a variety of different networks including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to be restrictive of the present disclosure. Further, the communications interface 138 can be configured to communicate with a single network or multiple networks across different access points.

In one specific embodiment illustrated in FIGS. 1G through 1I, the fiber optic sensor 100 can function as a fiber optic anemometer. In this embodiment, the transmitted light 140 (e.g., white-light centered at 1550 nm) is injected through the optical fiber 102 to the FP defined in the fiber optic sensor 100 by the optical fiber 102 and the silicon layer 108, and the reflection spectrum of the reflected light 162 can be recorded by a high-speed spectrometer 128. At the same time, heating light 142 from a heating light source 146 (e.g., 635 nm diode laser) can be guided through the same optical fiber 102 to the heat the FP. Silicon has a band gap energy of 1.11 eV and is highly transparent to the transmitted light 140 but is opaque to the heating light 142. Therefore, the FP temperature can be effectively increased by the heating light 142. When air moves (e.g., air convection 144) over the surface of a hot silicon layer 108, a cooling effect from the moving air reduces the temperature of the silicon layer 108 and the FP and introduces a shift to the fringe valley wavelength of the reflection spectrum, as schematically shown in FIGS. 1H and 1I. The wavelength shift can be separated by the spectrometer 128 and/or the controller 132 into a wind-temperature-induced wavelength shift and a wind-speed-induced wavelength shift. As a result, temperature self-compensated measurement of wind speed can be achieved by comparing the shift in the wavelengths of a fringe valley when the heating laser is turned on and off to determine temperature-compensated wind speed. It should be pointed out that although it is implemented as an anemometer in this example, it is not limited to measuring only the wind or air flow. Any other kind of flows (e.g., water flow) that can bring about the cooling effects to the heated sensor head can be measured.

FIG. 1J illustrates an embodiment of a fiber-optic sensor 100 that comprises a bolometer. As described above, a bolometer measures or detects power flux from electromagnetic radiation or particles by the heating of the respective material. In this embodiment, a Fabry-Pérot interferometer (FPI) is coupled to the end face 152 of an optical fiber 102. The FPI can be formed by a silicon pillar (e.g., silicon layer 108) with a first side of the silicon pillar coated with an absorptive and reflective layer (e.g., coating) 112 and the other side (e.g., a side distal from the first side and proximate to the end face 152) with reflective dielectric thin film 110. It is contemplated that absorptive coating 112 can include multiple metal coatings with the same or different materials. It is also contemplated that the reflective dielectric thin film 110 can include multiple layers of the same or different materials. The FPI can be connected to the end face 152 on the reflective dielectric thin film 110 side. The reflective dielectric thin film 110 serves as a mirror for the FPI. The absorptive coating 112 functions both as a second mirror for the FPI and as an absorptive element that absorbs an incident signal 116 and conducts heat to the silicon pillar. The choice of absorptive coating 112 material and thickness may be optimized to adjust the thermal properties of the combined pillar and its wavelength dependent absorptivity. Signals that penetrate through the absorptive coating 112 can also contribute to the heating of the silicon pillar but do not perturb its operation as an FPI. The heating of the silicon pillar increases the optical length if the FPI via increasing both the refractive index and the physical length of the silicon pillar through, respectively, the thermal optic effect and the thermal expansion of silicon material. The change in the optical length of FPI shifts the interferometric fringes in the reflection spectrum of the FPI, which can be measured by the light guided to the FPI through the optical fiber 102. The two mirrors (e.g., reflective dielectric thin film 110, absorptive coating 112) with high reflectivity can yield a large Finesse and narrow spectral features of the FPI, leading to high resolution in determining the wavelength shift of the fringes. The transmitted light 140 (e.g., light from a light source 126) should have wavelengths transparent to the silicon pillar. In one implementation, the transmitted light 140 wavelength is the 1550 nm window where a large of low-cost fiber-optic components and devices are available.

The fiber optic sensor 100 parameters, including the type and thickness of the absorptive coating(s) 112, the thickness of the silicon pillar, the reflectivity of the reflective dielectric thin film 110, can be optimized for different applications. For example, the absorptive coating 112 may include a gold metal coating, which serves as an excellent mirror with a reflectivity >95% over a broad wavelength range. A few micrometer gold coating can serve as good absorptive element from x-ray to the short end of the visible. Another choice of the metal may include platinum, which is commonly used in electronic resistive bolometers as the absorptive element. The thickness of the silicon pillar and the metal film can be designed to maximize the sensitivity in terms of minimally resolvable power of the incident signal.

Another function of the optical fiber 102 is to provide a thermal reservoir to the FPI. The optical fiber 102 can include specialty fibers to tune the performance of the bolometer. For example, the optical fiber 102 may include microstructured fibers, photonic crystal fibers, or side-hole fibers to tune the speed and sensitivity of the bolometer. For example, FIGS. 1K and 1L illustrates a specific optical fiber 102 that includes a side hole fiber, with cladding 106 that has at least one cavity 114 (e.g., an empty hole or space) along at least a portion of the length of the optical fiber 102. The at least one cavity 114 can be disposed proximate to an end face in the optical fiber 102. The cavities 114 effectively reduces the thermal conductivity of the fiber optic sensor 100. Because of the cavities 114, the heat transfer from the FPI to the optical fiber 102 becomes less efficient; therefore, increasing the sensitivity of the bolometer but reducing its speed. In some implementations, as shown in FIG. 1M, the cavity 114 can be filled with a thermal conductor 118 (e.g., thermal conductive medium), such as metal, that can help to dissipate the heat from the FPI to the optical fiber 102 to reduce the sensitivity and increase the speed of the fiber optic sensor 100.

FIG. 1M illustrates a specific embodiment where the fiber optic sensor 100 includes a mirror coating 122 dedicated as a highly reflective mirror for the FPI. The mirror coating 122 can be disposed between the absorptive coating 112 for signal absorption and the silicon pillar (e.g., silicon layer 108). In implementations, the mirror coating 122 may include a metal (e.g., gold) or a multilayer dielectric coating, similar to the reflective dielectric thin film 110 on the other side of the FPI. In instances where a mirror coating 122 includes a metal, a small amount of the light power can be absorbed to heat up the FPI (e.g., ~2% of light power can be absorbed by a mirror coating 122 including gold at about 1550 nm). As a result, the light power is maintained at a constant level. Otherwise, light power fluctuations may change the FPI temperature and can be mistakenly explained as the changes of the radiation signal. When a dielectric mirror coating 122 is used, the absorption of the light power may be smaller than a metal mirror coating 122. In the specific embodiment illustrated in FIG. 1M, the absorptive coating 112 can function mainly for the absorption of the incident signal 116. In addition, materials other than metal can also be used for the absorptive coating 112. With the absorptive coating 112, in general, any material that can convert the power flux into heat may be used. For example, the absorptive coating 112 may include carbon, which can be used as an absorber for radio frequency waves.

FIG. 1N illustrates an embodiment where the fiber optic sensor 100 includes a graded-index (GRIN) lens 176 disposed between the optical fiber 102 and the silicon layer 108. The profile of the light beam in a regular single mode fiber is close to that of a Gaussian beam and the mode field diameter is usually small (e.g., less than 15 μm). As the light beam exits the optical fiber 102 and travels into the FPI, the diffraction, which can be more prominent for smaller light beam, may limit the finesse of the FPI. The fiber optic sensor 100 illustrated in FIG. 1N can increase the size of the light beam in the FPI and increase the finesse of the FPI using a graded-index (GRIN) lens 176, which may also include a short-section of GRIN multimode fiber (MMF), that is inserted between the silicon layer 108 and the optical fiber 102. The GRIN lens 176 (and/or the MMF) functions as a light collimator, which can expand the light beam size to reduce light diffraction and increase finesse.

FIG. 1O illustrates an embodiment where the fiber optic sensor 100 includes an optical fiber 102 with an expanded core 178 disposed proximate to and/or abutted against the silicon layer 108 and/or reflective dielectric thin film 110. In this embodiment, the core 104 of the optical fiber 102 can be gradually expanded resulting in an expanded core 178. As the core 104 is gradually expanded toward the expanded core 178, the light beam profile can be gradually enlarged. In implementations, the expanded core 178 can be obtained by locally heating the fiber to a high temperature.

Example Processes

The following discussion describes example techniques for utilizing a fiber optic sensor and fiber optic sensing system, such as the fiber optic sensor 100 and fiber optic sensing system 130 described in FIGS. 1A through 1M. FIG. 2A depicts an example process 200 for using a bolometer device 100.

As shown in FIG. 2A, a light source is caused to transmit light through a fiber optic to a fiber optic sensor (Block 202). In this implementation, controller 132 can cause light source 126 to transmit light (e.g., transmitted light 140) through optical fiber 102 and circulator 124 to fiber optic sensor 100. Controller 132 can control the duration and intensity that the light source 126 transmits the transmitted light 140. In some specific implementations, controller 132 can cause heating light source 146 to transmit heating light 142 through the optical fiber 102 to the fiber optic sensor 100 and the silicon layer 108 for providing heat.

Reflected light from the fiber optic sensor is received using a spectrometer (Block 204). The spectrometer 128 can receive the reflected light 162 and associated spectra, which can be recorded and/or analyzed by spectrometer 128 and/or controller 132.

An output from the spectrometer is analyzed based on the received reflected light (Block 206). In implementations, the controller 132 and/or the spectrometer 128 can analyze the reflected light 162 and the spectra to determine a wavelength shift in the spectra, which indicates a change in temperature. A variety of methods may be utilized to analyze and/or determine the wavelength shift in the spectra and for tracking the average wavelength. In a specific embodiment, analyzing an output from the spectrometer based on received reflected light can include using an average wavelength tracking method to further increase the resolution of wavelength and/or measurand.

The following discussion describes example techniques for fabricating a fiber optic sensor, such as the fiber optic sensor 100 described in FIGS. 1A through 1M. FIG. 2B depicts an example process 300 for fabricating the fiber optic sensor 100. FIGS. 3A through 3E illustrate a section an exemplary fiber optic sensor 100 during fabrication (such as the fiber optic sensors 100 described in FIGS. 1A through 1M).

FIG. 2B depicts an example process 300 for fabricating a fiber optic sensor 100. As shown in FIG. 2B, a silicon pillar is formed on a silicon substrate (Block 302). FIG. 3A illustrates forming at least one silicon pillar 150 that will function as a sensor head for the fiber optic sensor 100. In one specific implementation, a double-side-polished silicon wafer (e.g., 200 μm thick) can be bonded on top of another larger silicon wafer using a layer of photoresist 154. The larger silicon wafer can function as a silicon substrate 148 to facilitate the fabrication and later as a support for the fabricated silicon pillar 150. Then another layer of photoresist 154 can be coated on the top of the double-side-polished silicon wafer and patterned accordingly using photolithography techniques. The patterned top silicon layer can be etched all the way to the silicon substrate 148 and the second layer of photoresist 154 using, for example, deep-reactive-ion-etching, leaving the upstanding silicon pillar(s) 150 attached to the silicon substrate 148.

Then, a thin film adhesive is formed on a glass substrate (Block 304). In some specific embodiments, such as the one illustrated in FIG. 3B, an adhesive 156 including a thin film of UV-curable glue can be spin-coated on a piece of glass substrate 158. It is contemplated that forming a thin film adhesive 156 may include using other adhesives and/or other methods for depositing and/or forming the adhesive 156. In embodiments, the adhesive 156 may include a thin film adhesive (e.g., UV-curable glue, an epoxy-based adhesive, and/or a gel-based adhesive).

Shown in FIG. 3C, an end face of an optical fiber is pressed onto the thin film adhesive (Block 306). In implementations, the adhesive 156 can be transferred to a cleaved and cleaned end face 152 of an optical fiber 102 by pressing the end face 152 of the optical fiber 102 to the adhesive 156 on the glass substrate 158. Subsequently, the end face 152 and the adhesive 156 can be released from the glass substrate 158.

As illustrated in FIGS. 3D and 3E, the optical thin film adhesive on the end face is placed onto the silicon pillar to provide the fiber optic sensor (Block 308). The optical fiber 102 with the silicon pillar 150 (silicon layer 108) attached can be lifted from the silicon substrate 148 and the second layer of photoresist 154. Further, fabrication of the fiber optic sensor 100 may include cleaning residual photoresist 154 from the end of the silicon pillar 150 (e.g., with alcohol). Due to the ultra-thin thickness of the residual photoresist 154 between the optical fiber 102 and the silicon pillar 150/silicon layer 108, the reflection spectrum of the FP cavity within the fiber optic sensor 100 is not affected.

Then, the thin film adhesive is cured (Block 310). In implementations, the adhesive 156 can be cured, for example, by UV irradiation (e.g., UV light 160). It is contemplated that other bonding technology may be implemented to mount the silicon layer 108 (or other material) to the end face 152 of the optical fiber 102, such as physical contact bonding.

It is contemplated that the above steps may be repeated to form a fiber optic sensor 100 with cascaded Fabry-Pérot cavities. For example, the optical fiber 102 with the silicon pillar 150 may be further pressed onto a second adhesive 166 on a glass substrate, placed on a second silicon pillar (e.g., second silicon layer 168), and cured using UV light, to form a fiber optic sensor 100 with two Fabry-Pérot interferometers. Further Fabry-Pérot interferometers may be fabricated by repeating the above steps.

As described above, a first side (e.g., side or surface distal to the end face 152) of the silicon pillar 150/silicon layer 108 can be coated with an absorptive layer (e.g., coating) 112 and a second side (e.g., side or surface proximal or adjacent to the end face 152) of the silicon pillar 150/silicon layer 108 can be coated with a reflective dielectric thin film 110. Thus, as described above, suitable techniques can be employed to deposit (e.g., coat) the respective surfaces of the silicon pillar 150/silicon layer 108 with the respective absorptive layer (e.g., coating) 112 and/or the reflective dielectric thin film 110.

FIG. 2C illustrates an exemplary process 400 for fabricating a bolometer device 100. As shown in FIG. 2C, an optical fiber including a reflective dielectric film on a cleaved endface of the optical fiber is received (Block 402). FIG. 4A illustrates receiving at least one optical fiber 102 having a reflective dielectric thin film 110 disposed on a cleaved end of the optical fiber 102. In some instances, multiple optical fibers 102 can include the reflective dielectric thin film 110 for batch processes.

FIG. 2C illustrates forming at least one silicon pillar (Block 404). In implementations, forming at least one silicon pillar 150 (e.g., silicon layer 108) can include forming a silicon pillar 150/silicon layer 108 that will function as a sensor head for the fiber optic bolometer device 100. In one specific implementation, the at least one silicon pillar 150 can be prepared by patterning and DRIE etching a silicon wafer 148 with a selected thickness after which each silicon pillar 150 can be attached to the silicon wafer 148 main frame through very thin arms (see FIG. 4B). The patterned top layer of the silicon wafer 148 can be etched all the way through the silicon substrate 148 using, for example, deep-reactive-ion-etching (DRIE), leaving the upstanding silicon pillar(s) 150 attached to the silicon substrate 148. In some specific embodiments, the reflective dielectric thin film 110 can be deposited on the surface of the silicon wafer 148 instead of the optical fiber endface 152 before patterning and dry etching the silicon wafer 148.

Then, a thin film adhesive is placed on the reflective dielectric thin film (Block 406). In some specific embodiments, such as the one illustrated in FIG. 4C, an adhesive 156 including a thin film of UV-curable glue can be spin-coated on a piece of glass substrate 158. It is contemplated that forming a thin film adhesive 156 may include using other adhesives and/or other methods for depositing and/or forming the adhesive 156. In embodiments, the adhesive 156 may include a thin film adhesive (e.g., UV-curable glue, an epoxy-based adhesive, and/or a gel-based adhesive). The optical fiber 102 can then be dipped onto the adhesive 156 and the substrate 158 and removed.

As illustrated in FIG. 2C, the adhesive on the end face of the optical fiber is placed onto the silicon pillar (Block 408). As shown in FIG. 4D, the optical fiber 102 with the silicon pillar 150 (e.g., silicon layer 108) attached can be lifted from the silicon substrate 148. In a specific implementation, the optical fiber 102 with the adhesive 156 (e.g., UV glue) can be pushed and/or placed onto the silicon pillar 150 and exposed to UV light to cure the adhesive 156 so that the silicon pillar 150 is firmly attached to the optical fiber endface 152, after which the optical fiber 102 can be lifted up with the silicon pillar 150, where the silicon pillar 150 breaks/detaches from the silicon wafer 150 at the thin arm formed during initial etching.

Next, the silicon pillar is etched (Block 410). In this step, etching the silicon pillar 150 can include can include fine-tuning the thickness of the silicon pillar 150 using, for example, wet etching (e.g., wet enchant 172 as shown in FIG. 4E), to control the wavelength positions of the interferometeric fringes of the Fabry-Pérot interferometer within the bolometer device 100.

As illustrated in FIG. 2C, an absorptive coating is then placed on the silicon pillar (Block 412). In one specific embodiment, as shown in FIG. 4F, placing an absorptive coating 112 on the silicon pillar 150 can include applying a gold coating on the silicon pillar 150 on the optical fiber endface 152 using, for example, plating, sputtering, and/or other deposition processes.

It is contemplated that the above steps may be repeated to form a fiber optic sensor 100 with cascaded Fabry-Pérot cavities. For example, the optical fiber 102 with the silicon pillar 150 may be further pressed onto a second adhesive 166 on a glass substrate, placed on a second silicon pillar (e.g., second silicon layer 168), and cured using UV light, to form a fiber optic sensor 100 with two Fabry-Pérot interferometers. Further Fabry-Pérot interferometers may be fabricated by repeating the above steps.

Multiple bolometers can be assembled to form a 2-D array and several bolometers can share a single tunable laser for signal demodulation, as illustrated in FIG. 3. In this example, a tunable laser, such as a distributed feedback (DFB) laser diode or an external cavity semiconductor laser, is used and the bolometers that share this laser are made to have their spectral notches within the wavelength tunable range of the laser. The light from the laser is split into each of the bolometers through a fiber-optic coupler and the reflected light from each bolometer is guided to a photodetector through a fiber-optic coupler or fiber-optic circulator. A separate photodetector is needed for each bolometer. The wavelength of the tunable laser is tuned and the waveform in the time domain from the photodetector is converted to the wavelength-domain to obtain the reflection spectrum of the bolometer.

FIG. 2D depicts an example process 500 for demodulating the fiber optic bolometer device 100. Multiple fiber optic bolometer devices 100 can be assembled to form a 2-D bolometer array 170, and several fiber optic bolometer devices 100 can share a single tunable laser (e.g., light source 126) for signal demodulation, as illustrated in FIG. 5. As shown in FIG. 2D, a light source is caused to transmit light through a fiber optic to a fiber optic bolometer device array (Block 502). In this implementation, controller 132 can cause light source 126 to transmit light (e.g., transmitted light 140) through optical fiber 102 and circulator 124 to fiber optic bolometer device array 170. Controller 132 can control the duration and intensity that the light source 126 transmits the transmitted light 140. In a specific implementation, a light source 126 can include a tunable laser, such as a distributed feedback (DFB) laser diode or an external cavity semiconductor laser, and the fiber optic bolometer devices 100 in the fiber optic bolometer device array 170 that share the laser diode are configured to have their spectral notches within the wavelength tunable range of the laser diode. The transmitted light 140 from the light source 126 is split into each of the bolometers (four are illustrated in FIG. 5) through a fiber-optic coupler 124.

Reflected light from the fiber optic sensor is received using at least one photodiode (Block 504). In embodiments, the at least one photodiode 174 can be included in a spectrometer 128. The spectrometer 128 can receive reflected light 162 and associated spectra from each of the fiber optic bolometer devices 100, which can be recorded and/or analyzed by spectrometer 128 and/or controller 132. The reflected light 162 from each fiber optic bolometer device 100 can be guided to a photodetector 174 through a fiber-optic coupler or fiber-optic circulator 124. In general, a separate photodetector 174 is needed for each fiber optic bolometer device 100.

An output from the at least one photodiode is analyzed based on the received reflected light (Block 506). In implementations, the controller 132, the at least one photodiode 174, and/or the spectrometer 128 can analyze the reflected light 162 and the spectra to determine a wavelength shift in the spectra, which indicates a change in temperature. A variety of methods may be utilized to analyze and/or determine the wavelength shift in the spectra and for tracking the average wavelength. In a specific embodiment, analyzing an output from the spectrometer based on received reflected light can include using an average wavelength tracking method to further increase the resolution of wavelength and/or measurand. The wavelength of the light source 126 (e.g., tunable laser) can be tuned and the waveform in the time domain from each photodetector 174 can be converted to the wavelength-domain to obtain the reflection spectrum of each fiber optic bolometer device 100.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:
1. A fiber optic bolometer device comprising:
an optical fiber;

a silicon layer disposed on an end face of the optical fiber, the silicon layer comprising a first surface and a second surface, where the silicon layer comprises a Fabry-Pérot interferometer;

a reflective dielectric film disposed over the first surface of the silicon layer, the reflective dielectric film adjacent to an end face of the optical fiber; and an absorptive coating disposed over the second surface of the silicon layer, the second surface distal to the end face of the optical fiber.

2. The fiber optic bolometer device of claim 1, wherein the optical fiber comprises at least one of a microstructured fiber, a photonic crystal fiber, a polarization-maintaining fiber, or a side-hole fiber.

3. The fiber optic bolometer device of claim 1, wherein the optic fiber includes an expanded core disposed proximate to the end face of the optical fiber.

4. The fiber optic bolometer device of claim 1, wherein the silicon layer includes a silicon pillar.

5. The fiber optic bolometer device of claim 1, wherein the absorptive coating comprises at least one metal layer.

6. The fiber optic bolometer device of claim 5, wherein the at least one metal layer comprises at least one of gold or platinum.

7. The fiber optic bolometer device of claim 1, wherein the optical fiber includes a cavity disposed along at least a portion of the optical fiber and proximate to the end face of the optical fiber.

8. The fiber optic bolometer device of claim 7, wherein the cavity is at least partially filled with a thermal conductor.

9. The fiber optic bolometer device of claim 1, further comprising a mirror coating disposed between the optical fiber and the absorptive coating.

10. The fiber optic bolometer device of claim 9, wherein the mirror coating is disposed between the silicon layer and the absorptive coating.

11. The fiber optic bolometer device of claim 1, further comprising at least one of a graded-index lens or a section of graded-index fiber disposed between the end face of the optical fiber and the absorptive coating.

12. A method for fabricating a fiber optic bolometer device, comprising:
receiving an optical fiber including a reflective dielectric film on a cleaved endface of the optical fiber;
forming at least one silicon pillar;
placing an adhesive on the reflective dielectric film;
pressing the optical fiber with the adhesive onto the silicon pillar;
etching the silicon pillar; and
placing an absorptive coating on the silicon pillar.

13. The method for fabricating a bolometer device in claim 12, wherein the absorptive coating includes gold.

14. A method for demodulating a fiber optic bolometer device array, comprising:
causing a light source to transmit light through an optical fiber and a circulator to a fiber optic bolometer device array including at least one fiber optic bolometer device, where the at least one fiber optic bolometer device includes a silicon layer and an absorptive layer disposed on an end face of the fiber optic bolometer device;
receiving reflected light from the fiber optic bolometer device array using at least one photodiode; and
analyzing an output from the at least one photodiode based on received reflected light to obtain a reflection spectrum of the bolometer.

15. The method for demodulating a fiber optic bolometer device array of claim 14, wherein the optical fiber comprises at least one of a microstructured fiber, a photonic crystal fiber, a polarization-maintaining fiber, or a side-hole fiber.

16. The method for demodulating a fiber optic bolometer device array of claim 14, wherein the optic fiber includes an expanded core disposed proximate to the end face.

17. The method for demodulating a fiber optic bolometer device array of claim 14, wherein the optical fiber includes a cavity disposed along at least a portion of the optical fiber and proximate to the end face of the optical fiber.

18. The method for demodulating a fiber optic bolometer device array of claim 17, wherein the cavity is at least partially filled with a thermal conductor.

19. The method for demodulating a fiber optic bolometer device array of claim 14, further comprising a mirror coating disposed between the optical fiber and the absorptive coating.

20. The method for demodulating a fiber optic bolometer device array of claim 14, further comprising at least one of a graded-index lens or a section of graded-index fiber disposed between the end face of the optical fiber and the absorptive coating.

* * * * *